(12) United States Patent
Brone et al.

(10) Patent No.: US 7,651,007 B2
(45) Date of Patent: Jan. 26, 2010

(54) METHOD OF UNIFORMLY SUPPLYING A MIXTURE OF PARTICULATE SOLIDS

(75) Inventors: Dean Lance Brone, Ann Arbor, MI (US); Scott A. Clement, Atascadero, CA (US); Bruno Caspar Hancock, North Stonington, CT (US); David Bruce Hedden, Ann Arbor, MI (US); Michael A. McCall, Atascadero, CA (US); James K. Prescott, Shrewsbury, MA (US); Thomas G. Troxel, San Luis Obispo, CA (US)

(73) Assignee: Jenike & Johanson, Inc., Tyngsboro, MA (US)

( * ) Notice: Subject to any disclaimer, the term of this patent is extended or adjusted under 35 U.S.C. 154(b) by 118 days.

(21) Appl. No.: 11/906,948

(22) Filed: Oct. 3, 2007

(65) Prior Publication Data
US 2008/0028874 A1 Feb. 7, 2008

Related U.S. Application Data (62) Division of application No. 11/304,424, filed on Dec. 15, 2005, now Pat. No. 7,347,111.

(51) Int. Cl.
*B67B 7/00* (2006.01)

(52) U.S. Cl. .................. 222/1; 222/229; 73/863.56

(58) Field of Classification Search .................. 222/1, 222/229, 236–238, 504; 73/866, 866.1, 864.24, 73/863.45, 863.54, 863.56; 366/130, 134–136
See application file for complete search history.

(56) References Cited

U.S. PATENT DOCUMENTS

| | | | | |
|---|---|---|---|---|
| 27,582 | A * | 3/1860 | Van Gelder | 73/863.56 |
| 608,834 | A * | 8/1898 | Byrnes | 73/863.45 |
| 850,293 | A * | 4/1907 | Calkins | 73/863.45 |
| 1,238,058 | A * | 8/1917 | Backus | 73/863.56 |
| 3,392,491 | A | 7/1968 | Vogt | |
| 3,690,179 | A * | 9/1972 | Olson | 73/863.56 |
| 3,794,164 | A | 2/1974 | Ginaven | |
| 4,172,667 | A | 10/1979 | Zenz et al. | |
| 5,429,248 | A | 7/1995 | Le Gigan et al. | |
| 5,583,304 | A | 12/1996 | Kalidindi | |
| 6,487,921 | B1 | 12/2002 | Prescott et al. | |
| 7,240,575 | B2 | 7/2007 | Brone et al. | |

* cited by examiner

*Primary Examiner*—Lien T Ngo
(74) *Attorney, Agent, or Firm*—Morse, Barnes-Brown & Pendleton, P.C.

(57) ABSTRACT

A method makes use of a minimally-shearing feeder mechanism supplying a desired flow of particulate solids mixture, with minimal to no sifting segregation to a desired location. The feeder methodology maintains a uniform concentration of each size of particle within the mixture.

9 Claims, 12 Drawing Sheets

METHOD OF UNIFORMLY SUPPLYING A MIXTURE OF PARTICULATE SOLIDS

RELATED APPLICATIONS

This application is a division of and claims the benefit of U.S. patent application Ser. No. 11/304,424, filed Dec. 15, 2005 now U.S. Pat. No. 7,347,111, which is expressly and entirely incorporated herein by reference.

FIELD OF THE INVENTION

The present invention relates to a method of feeding particulate solids, and more particularly to a minimally-shearing feeder methodology that regulates and controls the supply of a particulate mixture received from a supply hopper.

BACKGROUND OF THE INVENTION

Mixtures of solid particles can separate or segregate during handling. The non-uniformity of the mixture can result in quality control problems, such as the waste of raw materials, lost production, and increased maintenance and capital costs required to retrofit existing facilities where unwanted segregation of solid particle flows is occurring. Segregation problems can occur with a number of different types of solid particle mixtures, including larger particles, such as coal or rocks, to smaller particles, such as powders, including pharmaceutical powders.

Segregation can occur in a number of different ways, based primarily on various physical properties of the mixture and environmental or handling conditions. Sifting is a prevalent form of segregation. Sifting can be defined as the movement of smaller particles through a mixture of larger particles. This can occur during formation of a pile, as smaller particles percolate into the pile, while coarse particles slide or roll to the perimeter of the pile. In order for sifting segregation to occur, several conditions are required. There must be a difference in particle size, for example, ratios as small as 1.3:1 can induce sifting segregation. Sifting is generally most pronounced when the mean particle diameter is greater than 100 microns. The mixture must be sufficiently free flowing to allow interparticle motion. Finally, there must be movement of the particles relative to one another or portions of the flow within the mixture.

Bulk storage containers, such as hoppers, silos, bunkers and bins, are conventionally used for the storage of quantities of loose particulate solids, including particulate solid mixtures. For the purposes of the present application, the term "hopper" will be used to cover all such differing forms of storage containers for particulate material, where the material fills or partially fills the container and moves during the discharge process to an outlet situated in the lower regions of the container. If all of the material is in motion during discharge, this is referred to as mass flow of the material.

Bulk solids are generally comprised of particles of different sizes. It is commonly desirable to maintain a uniform concentration of each size throughout the mixture during industrial processing, storage, and packaging. However, segregation of the particles by size frequently occurs during processing steps such as the filling or discharge of a hopper. Such actions can lead to segregation by sifting. Accordingly, different regions within a mixture of particulate solids within a hopper can have different proportions of fine and coarse particles. Thus, uniformity of the mixture is lost.

For numerous reasons it can be desirable to be able to handle and move bulk solids with different size particles while maintaining a uniform concentration of each size, including sampling, measurement, and testing processes as well as general handling of the material. Feeder mechanisms can be utilized to supply mixtures of bulk solids to hoppers or other locations.

SUMMARY OF THE INVENTION

There is a need for a feeder methodology that maintains a good mixture of solid particulates of different size and composition for processes such as segregation testing and the like. The present invention is directed toward further solutions to address this need.

In accordance with one embodiment of the present invention, a method of uniformly supplying a mixture of particulate solids includes receiving a supply of the mixture from a supply source. The mixture is directed to a deposition aperture configured to receive the mixture and deposit the mixture on a rotating plate in the form of a deposited trail as the rotating plate rotates. The deposited trail is displaced radially and progressively outwardly along the rotating plate to a plurality of pass through apertures disposed in the plate. The mixture is discharged from the plurality of pass through apertures and through a discharge aperture.

In accordance with aspects of the present invention, the supply source comprises a bin or hopper. The deposition aperture can be disposed in a fixed cam plate slidably mounted over the rotating plate. Displacing the deposited trail can include forming the deposited trail on the rotating plate with a uniform cross-sectional area. Displacing the deposited trail can further include using a fixed cam plate having a contoured periphery configured to displace the deposited trail radially and progressively outward to the plurality of pass through apertures of the rotating plate as the rotating plate rotates, supplying the mixture forming the deposited trail to the discharge aperture. The cam plate can be configured to displace the deposited trail radially and progressively outward with minimal shearing of the mixture forming the deposited trail.

In accordance with further aspects of the present invention, the method can include rotating the rotating plate at a rate that at least substantially hinders the mixture from arching over the plurality of pass through apertures. The rotating plate can rotate at a rate of between about 2 RPM and about 20 RPM. A motor can drive the rotating plate. The feeder can supply a substantially constant stream of the mixture through the discharge aperture.

BRIEF DESCRIPTION OF THE DRAWINGS

The present invention will become better understood with reference to the following description and accompanying drawings, wherein.

DETAILED DESCRIPTION

An illustrative embodiment of the present invention relates to a method of using a specialized feeder mechanism, which provides a steady minimally-shearing supply of the mixture to, for example, a channel hopper. The feeder mechanism can vary in speed, thus varying flow rate of the mixture as desired. The feeder mechanism further operates with minimal sifting segregation of the mixture as it passes through the feeder mechanism to the channel hopper. Prior to entering the feeder mechanism, the mixture is well mixed by some means unrelated to the apparatus of the present invention. The operation of feeding the mixture with the feeder mechanism from a supply hopper to the channel hopper for testing provides minimal disruption of the mixture, while simultaneously enabling regulation and control of the mixture feed to the channel hopper.

FIGS. 1 through 9, wherein like parts are designated by like reference numerals throughout, illustrate example embodiments of a particulate solids mixture segregation testing apparatus and corresponding method of use, and a feeder mechanism an method of use according to the present invention. Although the present invention will be described with reference to the example embodiments illustrated in the figures, it shall be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

Figure 1:
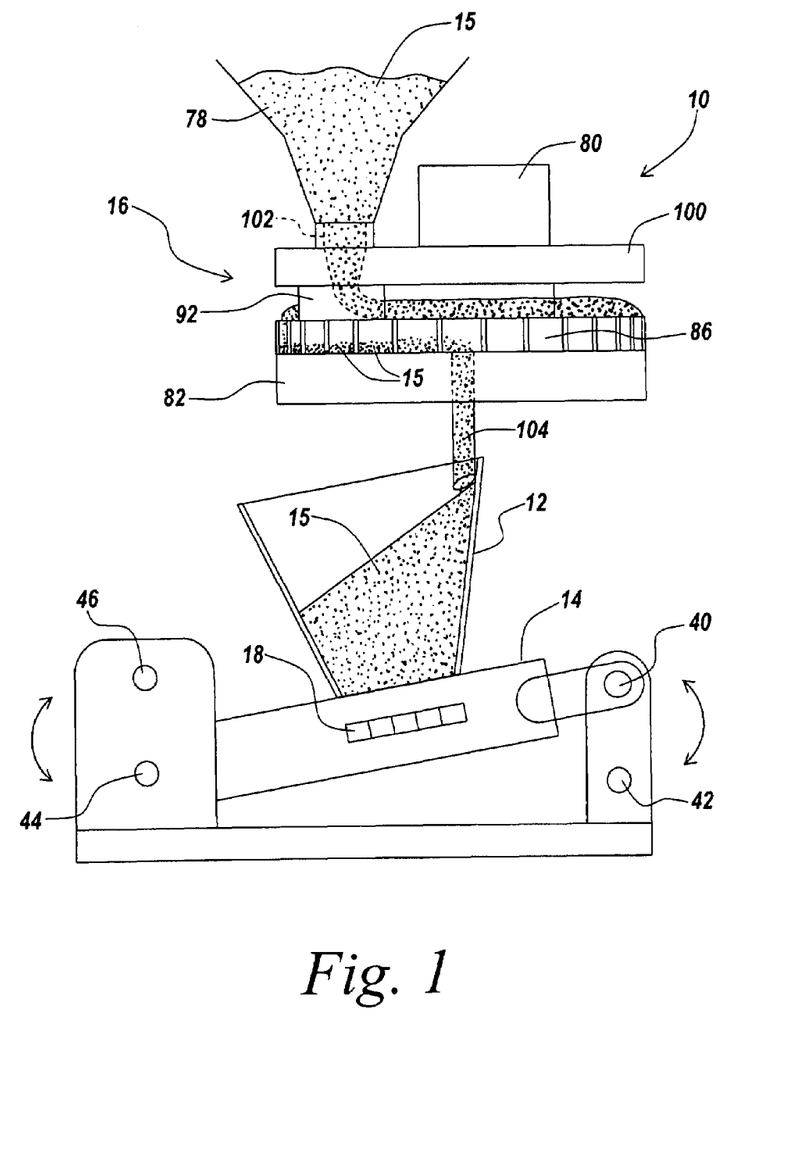
FIG. 1 is a diagrammatic illustration of a segregation testing apparatus, according to one embodiment of the present invention.

FIG. 1 is a diagrammatic illustration of a particulate solids mixture segregation testing apparatus 10 in accordance with one embodiment of the present invention. The testing apparatus 10 in its simplest form includes a channel hopper 12 and a sample collector 14. The channel hopper 12 is further depicted in FIG. 2, and the collector 14 is later described in multiple embodiments herein.

Generally, the channel hopper 12 receives a particulate solids mixture 15 from a feeder mechanism 16, stores the mixture to a predetermined level or amount in the channel hopper 12, and then conveys or channels the mixture 15 to the collector 14 formed of a plurality mixture sample receptacles 18. Additional details regarding this apparatus and process will be described in further detail below.

Figure 2:
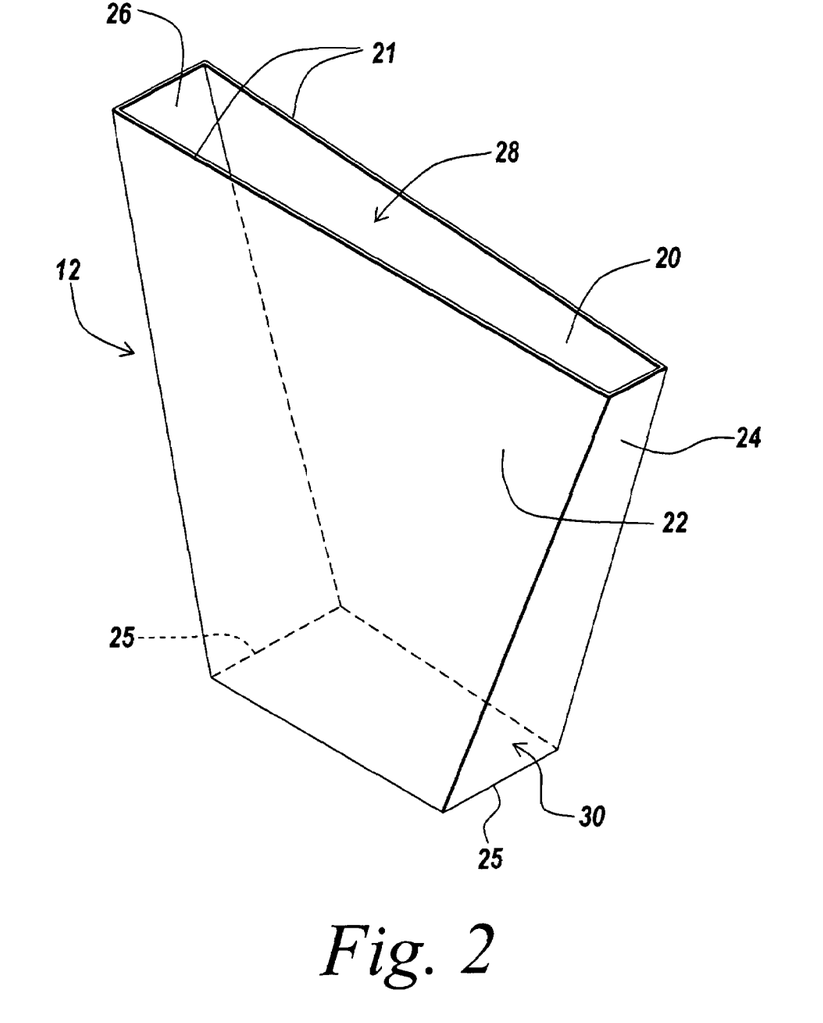
FIG. 2 is a perspective illustration of a channel hopper portion of the testing apparatus, according to one aspect of the present invention.

With regard to FIG. 2, the channel hopper 12 is depicted in accordance with one example embodiment of the present invention. The channel hopper 12 includes a first pair of opposed walls 21 formed of a first wall 20 and a second wall 22. The channel hopper 12 further includes a second pair of opposed walls 25 formed of a third wall 24 and a fourth wall 26. The first pair of opposed walls 21 and the second pair of opposed walls 25 couple together to create the channel hopper 12 with a supply opening 28 and a discharge opening 30. The supply opening 28 is sufficiently sized to enable supply of the mixture 15 to the channel hopper 12, and the discharge opening is sufficiently sized to enable discharge of the mixture 15 from the channel hopper 12, when desired. As depicted, the supply opening 28 and the discharge opening 30 extend across a complete length and width of the channel hopper 12. However, one of ordinary skill in the art will appreciate that the supply opening 28 and discharge opening 30 need not be as large relative to the channel hopper 12 size. Additional panels or walls can be provided to reduce their respective sizes, if desired. It shall further be noted that the discharge opening 30 can have a tapering rectangular shape. However, this is merely representative of one possible shape of the discharge opening 30 in accordance with one example embodiment of the present invention.

The channel hopper 12 is formed of a series of convergently and divergently angled walls. Looking at FIGS. 2, 3A, 3B, 3C, and 3D, one example embodiment of the channel hopper 12 is depicted to illustrate the convergent and divergent relationships. The first pair of opposed walls 21 are divergently angled relative to each other from the supply opening 28 toward the discharge opening 30. The purpose of the divergent relationship is to alter the stress field within the mixture during discharge from the channel hopper 12, to promote mass flow with reduced velocity gradients, in order to maintain the state of segregation as samples are collected. The actual degree to which the divergent angle relationship occurs can vary depending on the particular application and perhaps the specific mixture 15 being tested. However, generally, the divergent angle can be greater than about 1 degree from parallel to promote mass flow.

Figure 3A:
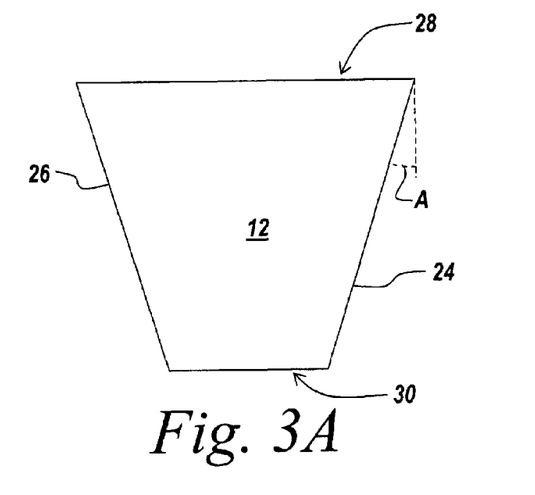
FIGS. 3A, 3B, 3C, and 3D are front view, top view, bottom view, and side view, respectively, of the channel hopper of FIG. 2, according to one aspect of the present invention.

The second pair of opposed walls 25 are convergently angled relative to each other from the supply opening 28 toward the discharge opening 30. The purpose of the convergent relationship is twofold. The third wall 24 (which is proximal to a supply point of the mixture 15 as later discussed) is angled relative to vertical by an amount represented by angle A. The function of angle A is to cause the third wall 24 to be at a sufficient angle such that mixture 15 supplied to the supply opening 28 proximal the third wall 24 slides along the first wall toward the discharge opening 30 and collects within the channel hopper 12 (the channel hopper having the discharge opening 30 blocked during the fill stage of the process, as later described). However, angle A should not be so large as to cause a significant velocity gradient of the mixture 15. Angle A should be sufficient to merely direct and maintain control of the flow of the mixture 15 to reduce the occurrence of bouncing, spraying, or other creation of airborne mixture particulates. Thus, angle A is sufficient to control the flow of the mixture into the channel hopper 12, but does not create a substantial hindrance to the flow of the mixture 15. As the channel hopper 12 sits flat, an example measurement of angle A that often provides the desired functionality is about 10-15 degrees from vertical. However, during the fill or supply of the mixture 15 to the channel hopper 12, the channel hopper 12 is pivoted (as later described) to cause angle A to reduce to about 5 degrees from vertical, in accordance with one example implementation.

The fourth wall 26, which makes up the other portion of the second pair of opposed walls 25 is also angled convergently. The purpose of a convergent slope for the fourth wall 26 is to provide a surface that can form plus or minus 20 degrees in the vicinity of a right angle with an angle of repose R (see FIG. 4)

when the channel hopper 12 is in its fill position, which may require a pivoting of the channel hopper 12 as later described. This geometry provides a relatively long sliding length for the mixture during a fill operation, while still providing a reasonably small outlet to collect appropriate sized samples.

Figure 3B:
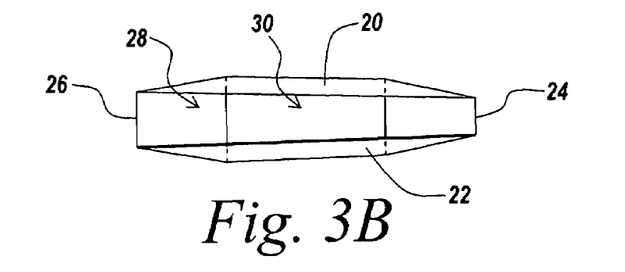
Figure 3C:
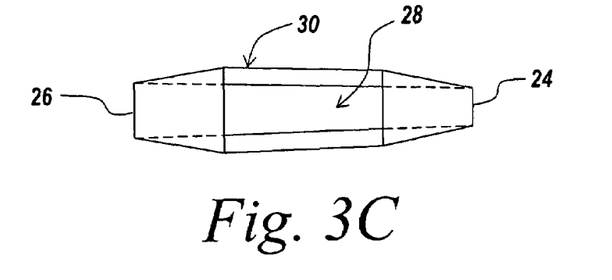
Figure 3D:
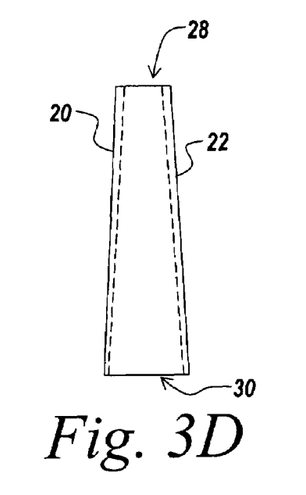

The first pair of opposed walls 21 are also divergently angled relative to each other from the third wall 24 toward the fourth wall 26, as can be seen in FIG. 3B. The purpose of the divergent relationship is to substantially minimize or eliminate the frictional surface effects of the first wall 20 and the second wall 22 on the flow of the mixture 15 as it is supplied to the channel hopper 12 and avalanches to a settled position. The actual degree to which the divergent angle relationship occurs can vary depending on the particular application and perhaps the specific mixture 15 being tested. However, generally, the divergent angle can be greater than about 1 degree from parallel to substantially minimize the frictional effects of the first and second walls 20 and 22 on the mixture. One result of the first pair of opposed walls 21 being divergently angled is that the supply opening 28 forms an elongate trapezoidal shape.

Briefly, and with reference to FIG. 1, the channel hopper 12 can have its overall orientation pivoted in one direction or the other. Specifically, a first pivot positioner 40, a second pivot positioner 42, a third pivot positioner 44, and a fourth pivot positioner 46, can work together to orient the channel hopper 12 as desired. As shown in the figure, the first pivot positioner 40 and the third pivot positioner 44 are being utilized to tilt or pivot the channel hopper 12 during a fill operation. The pivoting action enables the variation of the angle A (of FIG. 3A) relative to vertical, and also the variation of the slope of the opposite wall, namely the fourth wall 26, so that avalanching mixture 15 will approach the fourth wall 26 at about a perpendicular relationship. Then, after the fill operation is completed, the channel hopper 12 can be moved to the second pivot positioner 42 to orient the channel hopper 12 in a flat or horizontal orientation for sampling, as later described. One of ordinary skill in the art will appreciate that the first pivot positioner 40, second pivot positioner 42, third pivot positioner 44, and fourth pivot positioner 46 are merely representative of one example embodiment. The channel hopper 12 can be pivoted during the fill operation using only the third pivot positioner 44 and the first pivot positioner 40. If the channel hopper 12 is oriented in the opposite direction, or is filled on the opposite side, then the second pivot positioner 42 and the fourth pivot positioner 46 can work together to provide the appropriate pivot. Accordingly, one of ordinary skill in the art will appreciate that the illustrated embodiment merely demonstrates a number of different positioner options, not all of which are required in any one embodiment.

Returning now to FIGS. 3A-3D, the discharge opening 30 is formed by the combination of the first wall 20, the second wall 22, the third wall 24, and the fourth wall 26. The combination of the four walls of the channel hopper 12 can come together to form a rectilinear discharge opening 30, or a slightly trapezoidally shaped, or tapering rectangular shaped, discharge opening 30. The discharge opening is sized, dimensioned, and configured to support mass flow of the mixture through the channel hopper 12. Because the channel hopper 12 has a relatively smaller width, as viewed from the top, nearer the third wall 24 and a relatively larger width nearer the fourth wall 26, the discharge opening 30 can vary in width to allow less volumetric flow nearer the third wall 24 and more volumetric flow nearer the fourth wall 26. This is achieved by having a slight taper or alternatively a trapezoidal shape to the discharge opening 30, wherein the narrower end is proximal the third wall 24 and the wider end is proximal the fourth wall 26. Thus, as mixture flows through the channel hopper, there is preferably no change in flow velocity at the third wall 24 side of the channel hopper 12 relative to flow velocity at the fourth wall 26 side of the channel hopper 12. It shall be noted that if the cross-sectional area sliced through the channel hopper 12 at various horizontal locations is substantially the same (i.e., the convergent and divergent walls combine in some manner that results in a consistent length and width across a particular horizontal slice), then the discharge opening 30 can be a rectilinear shape. Furthermore, one of ordinary skill in the art will appreciate that the discharge opening 30 can take a number of different forms or shapes to adjust the mass flow rate of the mixture across all sections of the channel hopper 12 in accordance with concepts expressed herein.

Figure 4:
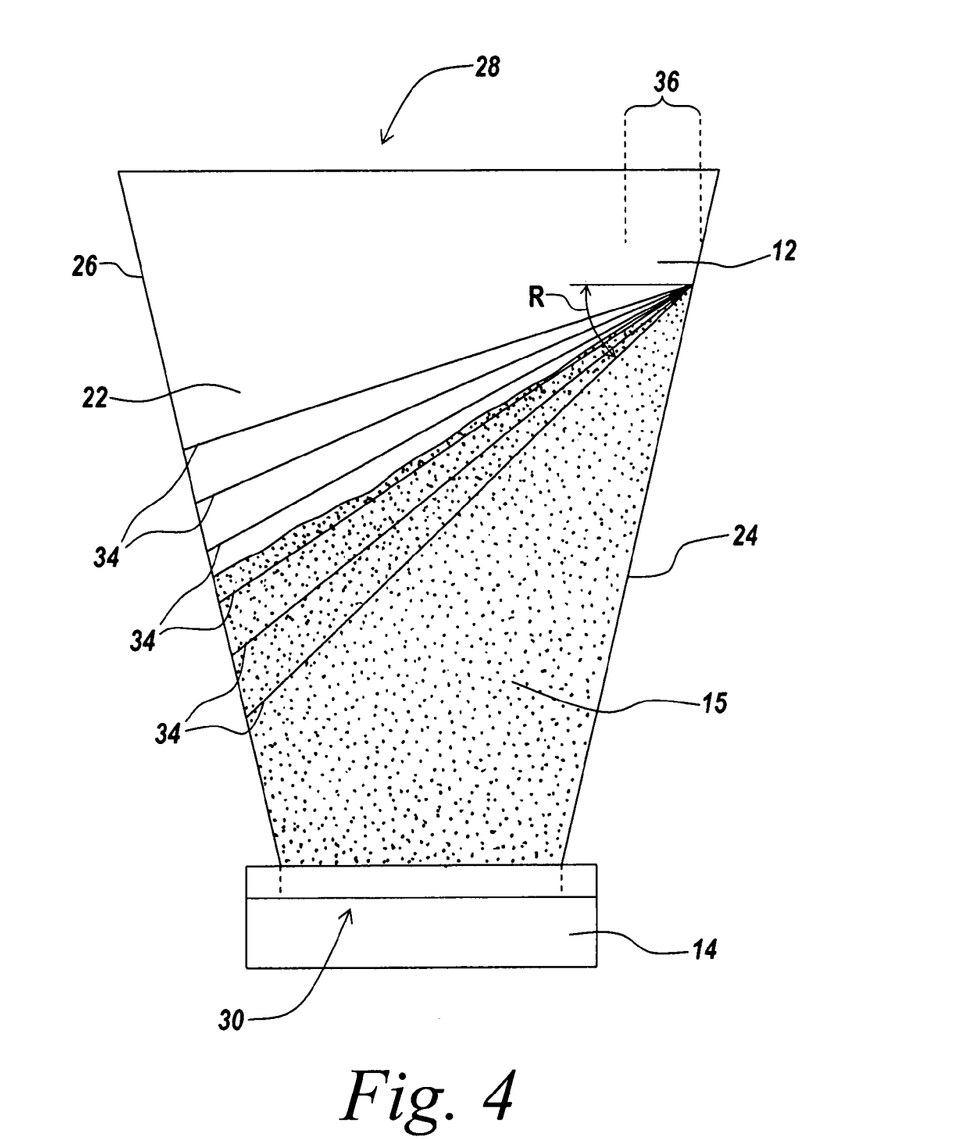
FIG. 4 is a diagrammatic illustration of the channel hopper partially filled with mixture for testing, according to one aspect of the present invention.

FIG. 4 is a diagrammatic front view illustration of the channel hopper 12 in accordance with one embodiment of the present invention. This figure shows the channel hopper 12 partially filled with mixture 15. The mixture 15 is provided to the channel hopper 12 at a fill region 36, which is essentially proximal the third wall 24, such that the mixture 15 can slide down the third wall 24 to fill the channel hopper 12 during a fill operation. The mixture 15 fills the channel hopper 12 by sliding down the third wall 24 and impacting with previously supplied mixture, then avalanching down toward the fourth wall 26. As the mixture avalanches, it does so at an angle of repose R related to the particular properties of the mixture 15, and the angle at which the channel hopper is oriented or pivoted. The channel hopper 12 can be substantially transparent, enabling a user to view the mixture 15 as it collects in the channel hopper 12. As such, the channel hopper 12 can additionally support use of angle of repose markings 34 so that a user may quickly reference the angle of repose. The angle of repose markings 34 can indicate, for example, angle measurements of between about 20 degrees and about 45 degrees from horizontal during a filling operation when the channel hopper 12 is pivoted.

Figure 5:
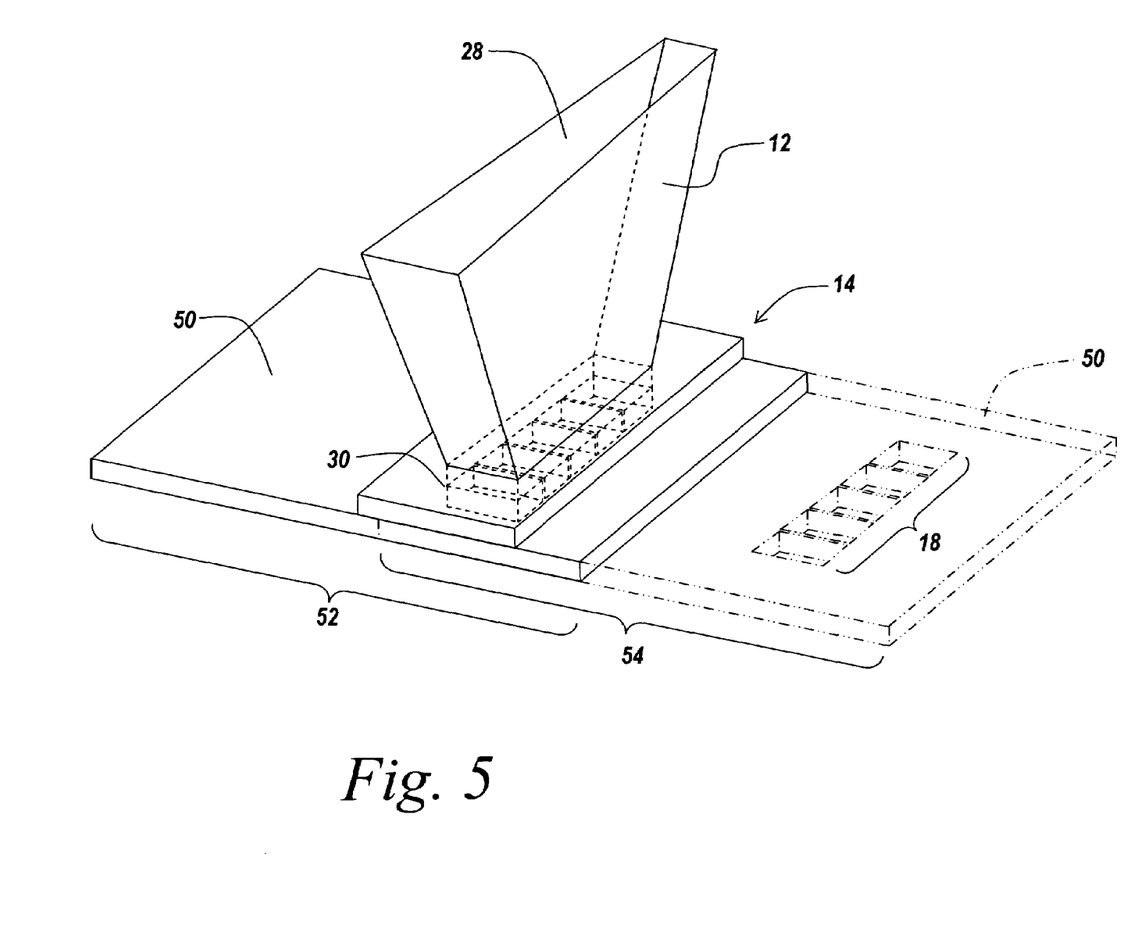
FIG. 5 is a perspective illustration of a collector portion of the testing apparatus, according to one aspect of the present invention.

When the channel hopper 12 has a sufficient amount of mixture 15 contained therein, a series of samples of the mixture 15 can be taken using the plurality of mixture sample receptacles 18 disposed in the collector 14 to receive mixture supplied to the channel hopper 12 for analysis of mixture segregation. Turning now to FIG. 5, the collector 14 and the plurality of sample receptacles 18 are shown in accordance with one example embodiment of the present invention. The sample receptacles 18 are resident within a shuttle 50. The shuttle 50 is reciprocally slidable between a first position 52 and a second position 54. When the shuttle is disposed in its first position 52, the plurality of sample receptacles are disposed beneath the discharge opening 30 of the channel hopper 12, enabling the mixture 15 to flow from the channel hopper 12 to the plurality of sample receptacles 18. The sample receptacles 18 are broken into five sections or segments in the illustrative embodiment. However, one of ordinary skill in the art will appreciate that a greater or fewer number of sample receptacles can form the plurality of sample receptacles 18 to vary the granularity of the sample rate.

As the mixture 15 flows into the plurality of sample receptacles 18, the plurality of sample receptacles fills until it is full, thus stopping mixture flow. The shuttle is then moved to the second position 54 where the user has access to the plurality of sample receptacles 18 and can remove the mixture 15 samples from each of the plurality of sample receptacles 18 for segregation testing. When the shuttle 50 is in the second position 54, the shuttle 50 acts as a channel block, blocking the discharge opening 30 of the channel hopper 12 so that no mixture 15 can flow. The process is repeated with the shuttle 50 reciprocating between first and second positions 52 and 54 to remove samples of the mixture 15 from the channel hopper 12 until all of the mixture 15 is removed from the channel hopper 12, or alternatively, until a sufficient amount is removed for the desired testing procedure. The arrangement of the samples receptacles allows for matrix sampling (rows and columns) by the test apparatus, if desired.

FIGS. 6, 6A, 6B, 6C, 6D, and 6E are illustrations of an alternative, and more elaborate, implementation to the collector 14 depicted in FIG. 5. In the present example, a collector 14' provides a more automated approach to obtaining the samples of the mixture 15 from the channel hopper 12. The configuration depicted also eliminates free-fall from the channel hopper 12 into the collector 14, and eliminates counter-flow of air up through the channel hopper 12, which can otherwise disrupt the segregation pattern in the channel hopper 12. The channel hopper 12 is not shown in this figure, but sits positioned atop a fixed base 56 as in other described implementations. A piston channel block 58 is sized and dimensioned to snugly fit within a first receptacle 62 of a first shuttle 60 (see FIG. 6A) passing through a piston receptacle or second receptacle 65 of a second shuttle 64. When it is desired for the mixture 15 to flow from the channel hopper 12 to be sampled, the piston channel block 58 lowers into the second receptacle 65 to reveal the first receptacle 62 (see FIG. 6B). The mixture 15 fills the first receptacle 62. The first shuttle 60, the second shuttle 64, and the piston channel block 58 (disposed in the second receptacle 65) reciprocally slide to close the discharge opening 30. The second shuttle 64 and the piston channel block 58 are then fixed in place, while the first shuttle 60 with the mixture 15 in the first receptacle 62 continues to reciprocally slide (see FIG. 6C). The mixture 15 transfers from the first receptacle 62 to a plurality of sample receptacles 18 in a third shuttle 68 (see FIG. 6D). The third shuttle 68 then reciprocally slides over each of a plurality of staggered apertures 72 in a fixed plate 70. As the third shuttle 68 slides over the staggered apertures 72, each individual receptacle of the plurality of sample receptacles 18 deposits the sample mixture 15 into one of a plurality of collection containers 74 (see FIG. 6E). Thus, the plurality of staggered apertures 72 aligns with the plurality of mixture sample receptacles 18 to incrementally enable flow of mixture from each of the plurality of mixture sample receptacles 18 one at a time into separate collection containers 74 as the third shuttle 68 slides over the fixed plate 70.

Figure 6:
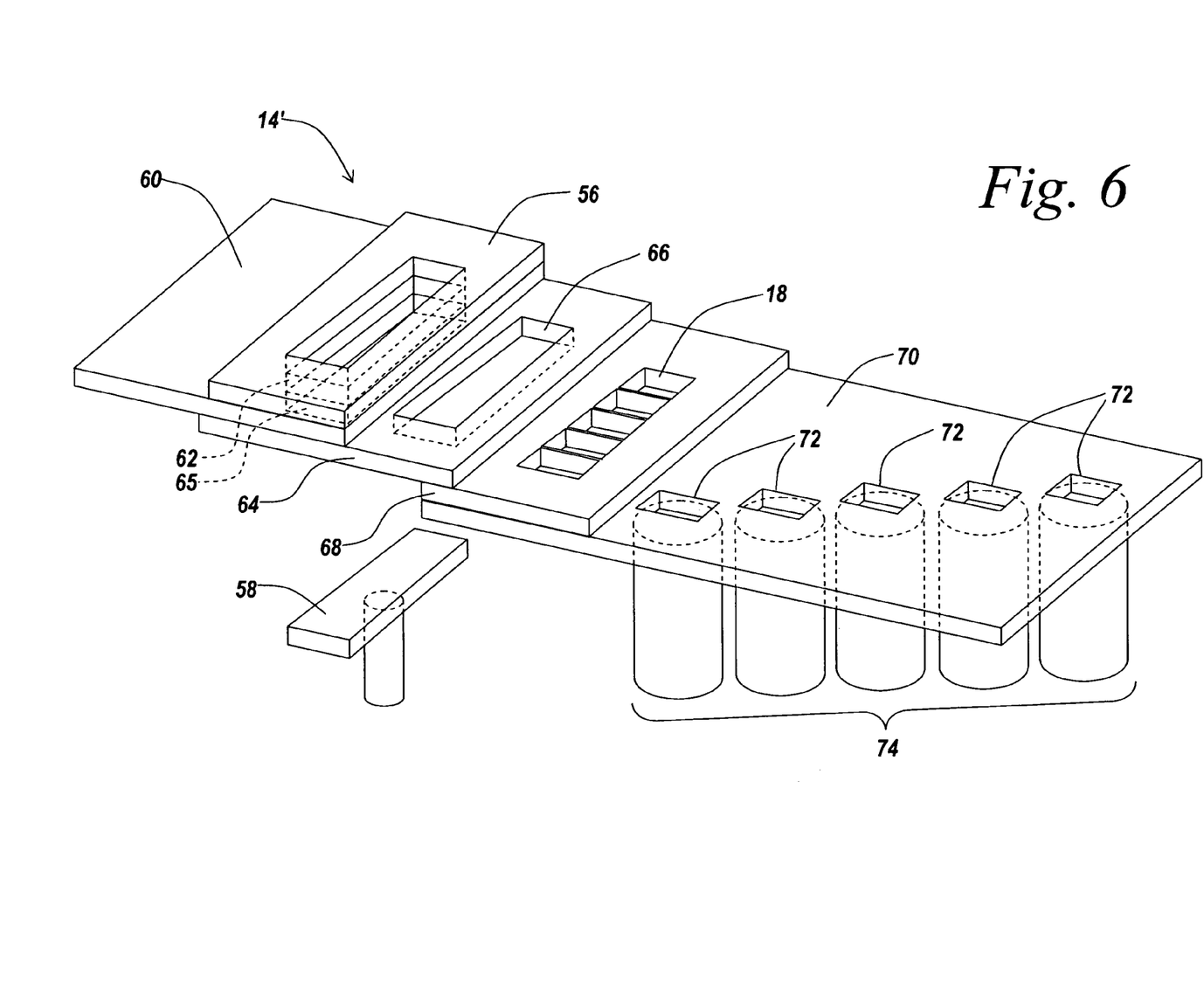
FIG. 6 is a perspective illustration of an alternative collector portion of the testing apparatus, according to one aspect of the present invention.
Figure 6A:
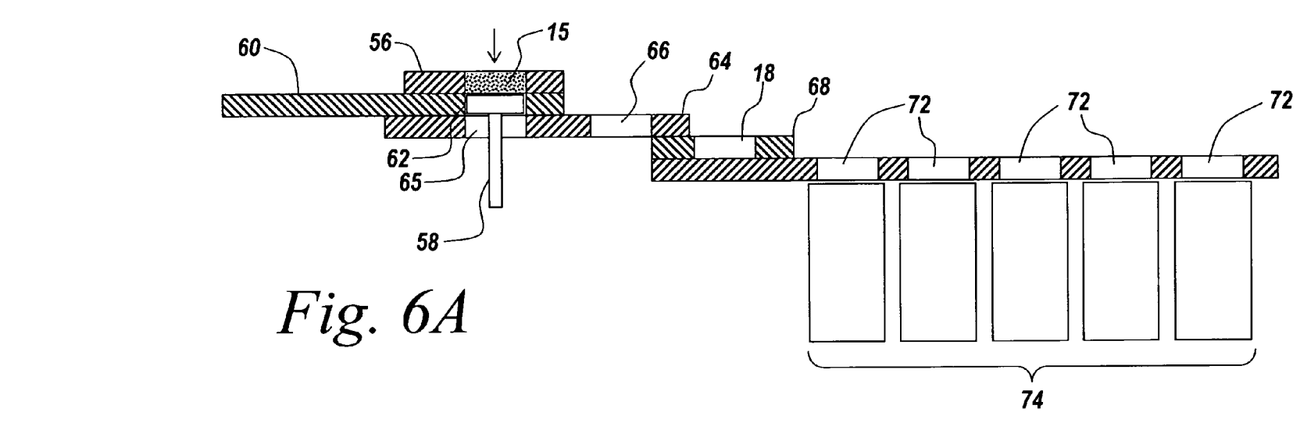
FIGS. 6A, 6B, 6C, 6D, and 6E are side view illustrations of the collector portion of FIG. 6, according to one aspect of the present invention.
Figure 6B:
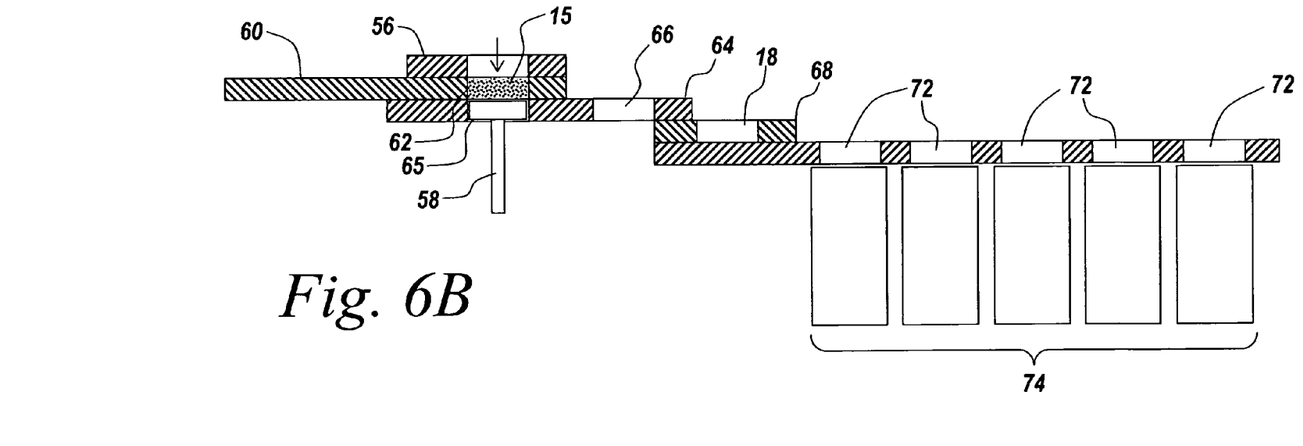
Figure 6C:
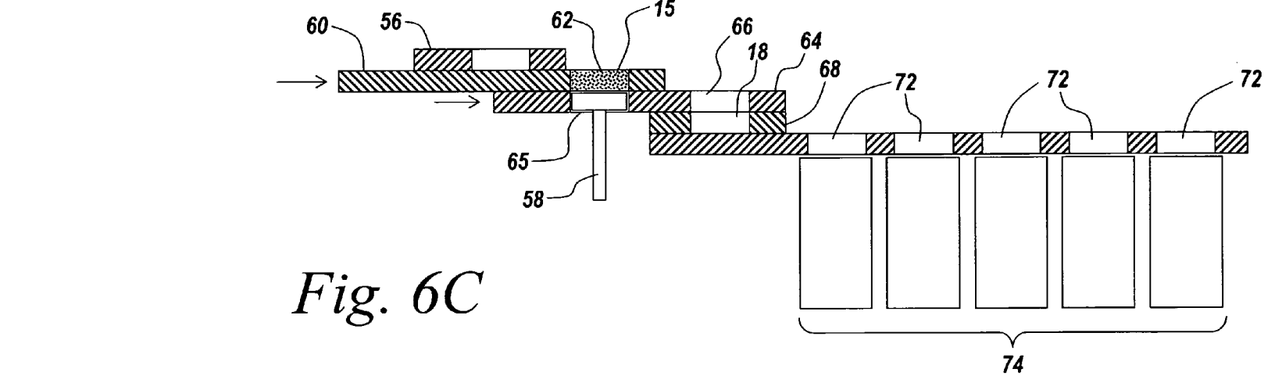
Figure 6D:
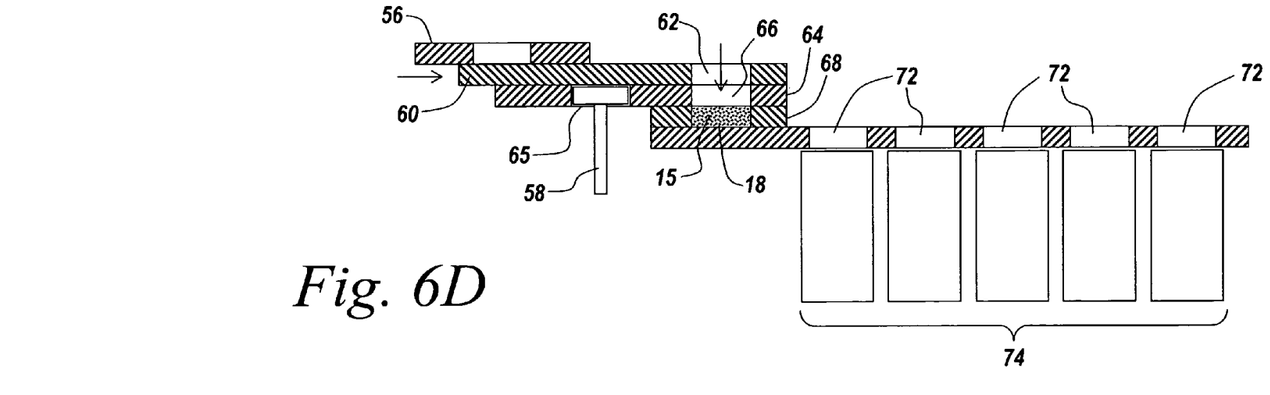
Figure 6E:
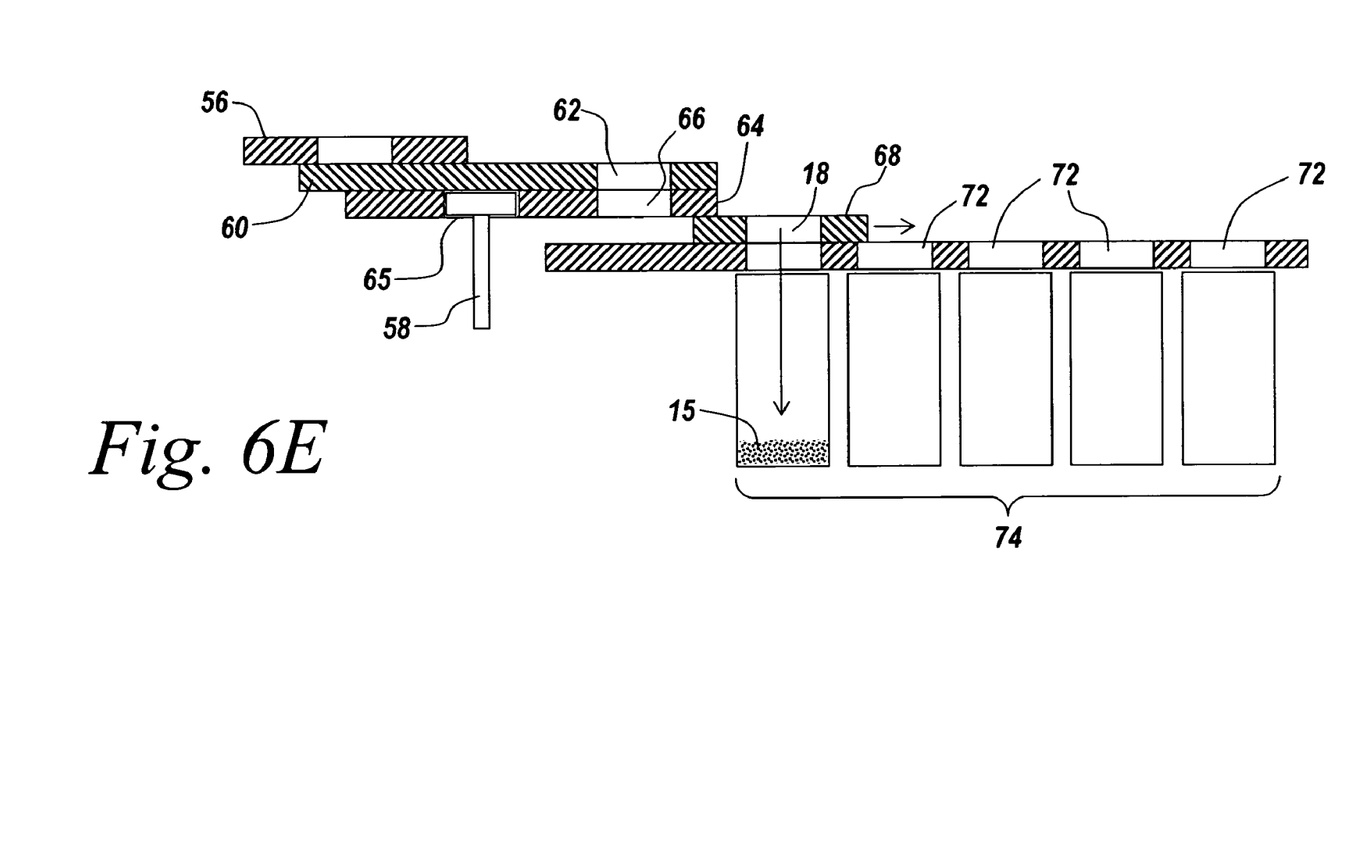

The mixture samples in each of the collection containers 74 can then each be analyzed for segregation or other testing. The first shuttle 60, the second shuttle 64, the third shuttle 68, the fixed plate 70, and the piston channel block 58 then reset to the positions shown in FIG. 6 to prepare for the next sampling of mixture 15 from the channel hopper 12. The return sequence is different from the initial sequence. The third shuttle 68 returns to its original position. The piston channel block 58 rises to fill the first receptacle 62 making the top face of the piston channel block 58 flush with the top of the first shuttle 60. Then, the first shuttle 60 and second shuttle 64 return to their original starting position. In this manner, the mixture 15 does not free-fall into the first receptacle 62. One of ordinary skill in the art will appreciate that the example of FIG. 6 is merely an alternative and more elaborate collection mechanism relative to the mechanism shown in FIG. 5. However, the present invention is not limited to the two variations of mechanisms described herein. These are simply intended as illustrative of mechanisms or devices that can form a part of the testing apparatus of the present invention to aid in the acquisition of mixture samples from the channel hopper 12 in a manner that is predicable, repeatable, and can obtain samples without substantially disrupting the mixture 15 in the channel hopper 12.

The collectors 14 and 14' of FIGS. 5 and 6 are useful in that they can repeatedly remove samples of mixture 15 from the channel hopper 12 without substantially disturbing or disrupting the physical position of the solid particles of the mixture relative to one another as they came to rest in the channel hopper 12. One of ordinary skill in the art will appreciate that other methods for removing the mixture 15 from the hopper may be more disruptive of the mixture 15. For example, if the mixture is scooped out from the supply opening 28 of the channel hopper 12, then the location of the removed mixture 15 would be filled in with additional avalanching of the mixture 15, thus highly disrupting the mixture 15. Alternatively, if the channel hopper 12 were tilted to pour the mixture 15 from the supply opening 28, again the mixture 15 as it settled or collected in the channel hopper 12 would be completely re-mixed and re-distributed. As such, accurate samples of how the mixture 15 came to rest within the channel hopper 12 would not be obtainable. The inventors of the present invention have devised the collectors 14 and 14' as described and depicted herein to remove mixture samples from the discharge opening 30 of the channel hopper 12 in a manner that maintains sufficient order of solid particles in the mixture 15 as they are deposited during the fill operation of the channel hopper 12. In so doing, the segregation pattern developed within the channel hopper 12 is maintained during the sample collection process. The collectors 14 and 14' further provide the ability to sample the entire mixture 15 contained in the channel hopper 12, in that repeated horizontal levels of mixture samples can be removed until the entire mixture 15 is removed from the channel hopper 12. Thus, the samples are highly demonstrative of the actual segregation of particles within all portions or locations of the channel hopper 12.

The testing apparatus 10 of the present invention as depicted in FIG. 1 further includes the feeder mechanism 16. In order to ensure a more accurate test of the segregation of solid particles in a mixture 15 as a result of being loaded into a bin or hopper, it is useful to maintain a good mixture of the solid particles as they are fed to the channel hopper 12. It can be desirable to maintain a steady controlled feed of the mixture 15 to the channel hopper 12. Mixtures of solid particles can have varying pockets of larger or smaller particles if not well mixed. In addition, some feeding mechanisms can cause shearing of the solid particles, breaking them up into half particles or smaller particles, which can be undesirable. In addition, some mixtures of solid particles can have relatively high cohesive strengths. The cohesive strength of a powder is a measure of the forces of attraction between the molecules. Mixtures with high cohesive strengths can be subject to clumping of the mixture. Accordingly, a feeder mechanism 16 is required that can maintain a mixture in its well-mixed condition while distributing or supplying a measurable or predicable amount of the mixture 15 to the channel hopper 12 for collection and subsequent testing. The feeder mechanism 16 should also operate with minimal shearing of the particles of the mixture 15 during distribution.

Figure 7:
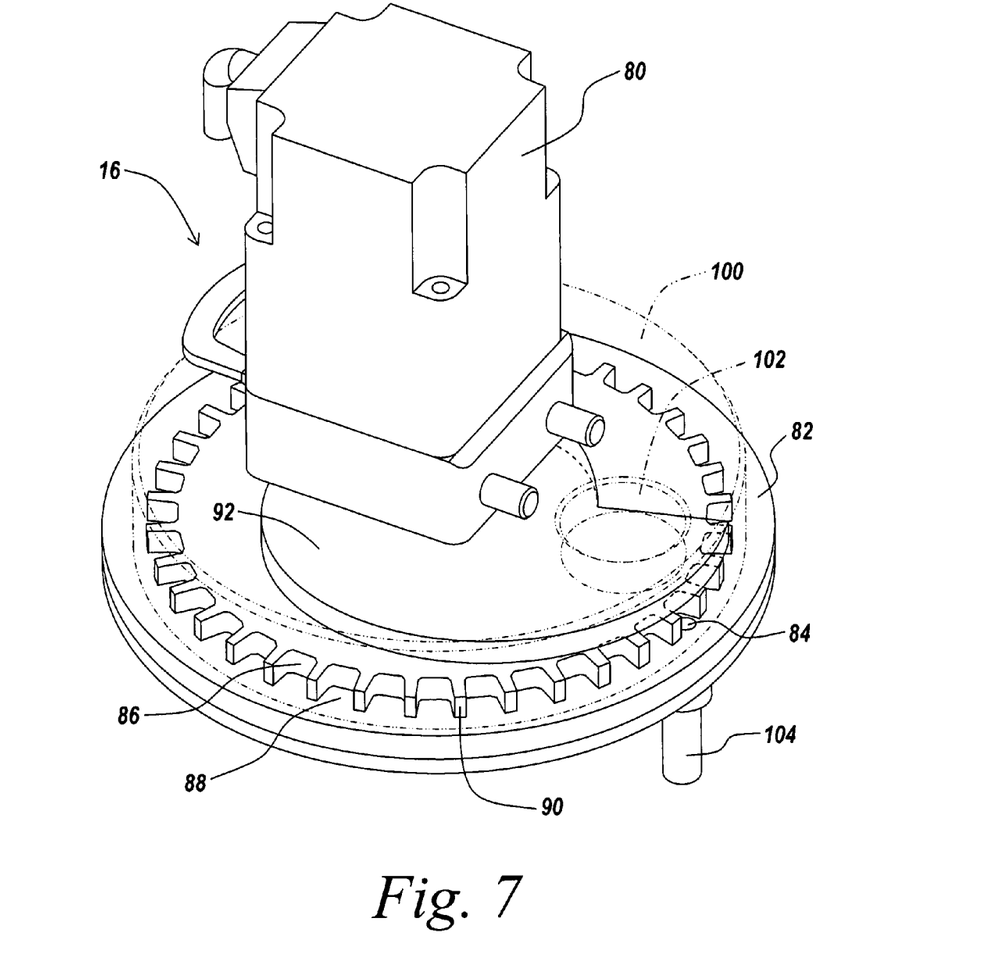
FIG. 7 is a perspective illustration of a feeder mechanism portion of the testing apparatus, according to one aspect of the present invention.
Figure 8:
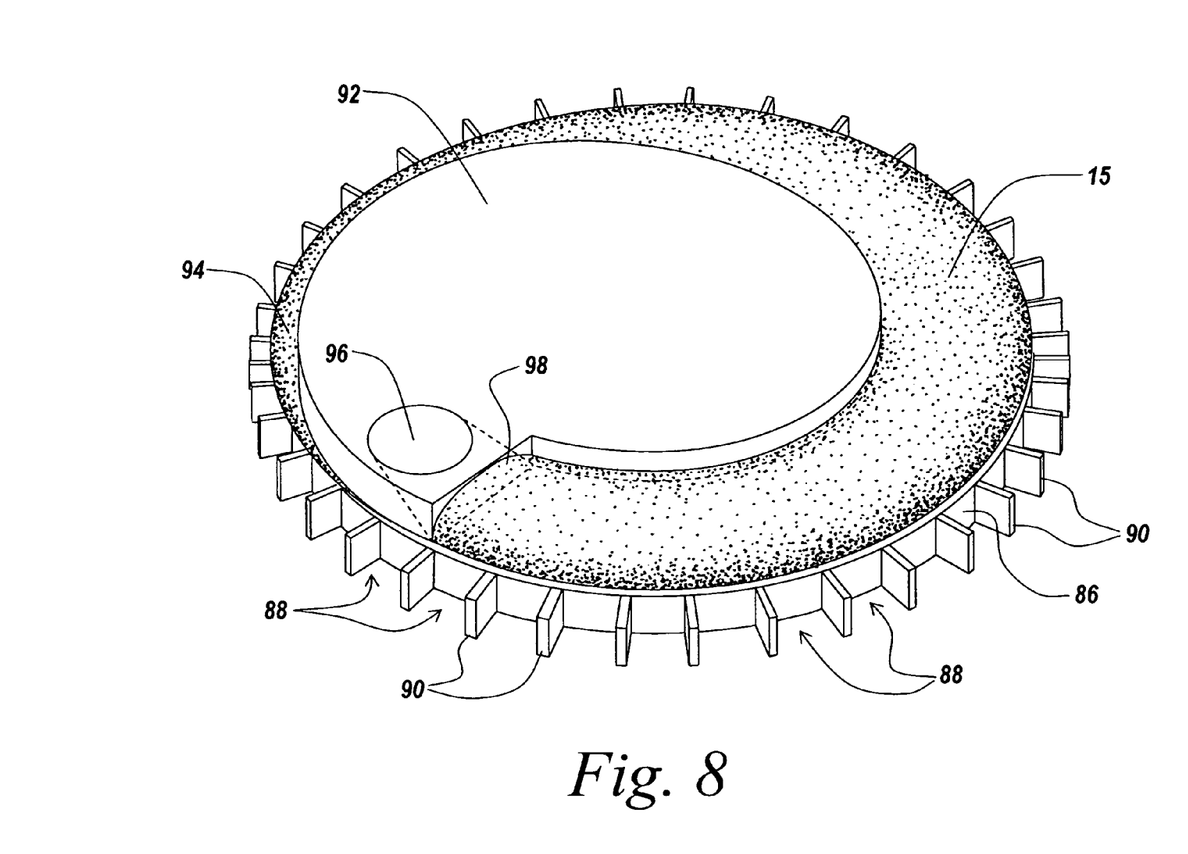
FIG. 8 is a perspective illustration of a cam portion of the feeder mechanism of FIG. 7, according to one aspect of the present invention.

Accordingly, the feeder mechanism 16 is depicted in FIGS. 1, 7, and 8, in accordance with one example embodiment of the present invention. The feeder mechanism 16 is a minimally-shearing mechanism that regulates and controls the supply of the mixture 15 from the supply hopper 78 where the mixture is well mixed, to the channel hopper 12 of the testing apparatus 10. The feeder mechanism 16 includes a motor 80 for powering the feeder mechanism 16. A fixed bottom plate 82 supports a rotatably slidable second plate 86. The fixed bottom plate 82 includes a discharge aperture 84, which provides the mixture 15 to a fill tube 104 that is ultimately positioned in the fill region 36 of the channel hopper 12.

The rotatably slidable second plate 86 includes a plurality of pass through apertures 88 formed with a plurality of dividers 90. In the example embodiment illustrated, the plurality of pass through apertures 88 are disposed about a periphery of the second plate 86, which is substantially circular in shape. However, one of ordinary skill in the art will appreciate that the plurality of pass through apertures 88 can take the form of complete holes drilled through the second plate 86, or some other variation that enables an aperture that passes completely through the second plate 86 in a manner that the mixture 15 can pass through as desired. Furthermore, the shape of the second plate 86 is not required to be circular, especially if the second plate 86 continues outwardly beyond the path of pass through apertures 88. Accordingly, the present invention is not limited to the specific implementation depicted herein. Rather, other equivalent structures are anticipated by the present invention, and are therefore included within the scope of the present invention.

Referring to FIG. 8, a fixed cam plate 92 is mounted on top of the second plate 86, in a manner allowing the second plate 86 to rotate relative to the cam plate 92. The fixed cam plate 92 has a contoured periphery 94 formed by an incrementally increasing radial dimension from an inner radius to an outer radius, the outer radius placing the contoured periphery or perimeter of the cam at about the location of the plurality of pass through apertures 88, such that any mixture deposited on the second plate 86 is pushed outward to the plurality of pass through apertures 88, and the cam plate 92 at its outermost radial dimension covers the top surface plate portion of the second plate. Further discussion of this relationship is provided below. The fixed cam plate 92 further includes a supply port 96 that leads to a deposition aperture 98. The supply port 96 couples with the supply hopper 78 and passes the mixture to the deposition aperture 98. The deposition aperture 98 deposits the mixture on the second plate 86 with a uniform cross-sectional area. The uniform cross-sectional area enables accurate regulation and control of the amount of mixture 15 ultimately being supplied to the channel hopper 12. The cross-sectional area created by the deposition aperture 98 is sized to regulate the flow rate to be below that provided by the pass through apertures 88 to prevent overfilling of the pass through apertures 88.

A fixed top plate 100 is disposed on top of the fixed cam plate 92 and supports the motor 80. The fixed top plate 100 further includes a supply aperture 102 that couples the supply hopper 78 with the supply port 96 of the fixed cam plate 92, enabling supply of the mixture to the deposition aperture 98.

Figure 9:
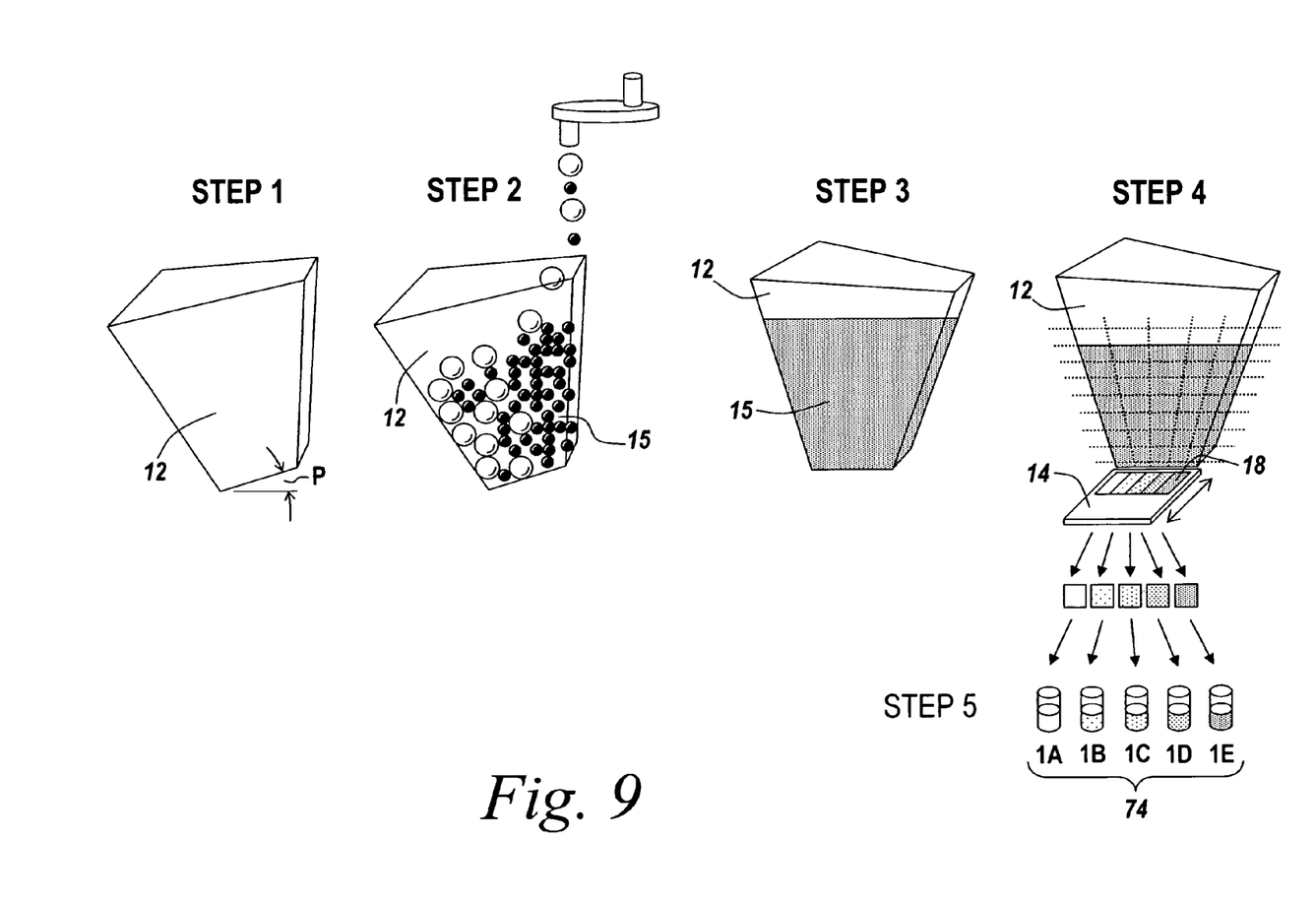
FIG. 9 is a diagrammatic illustration of a basic sampling procedure, according to one aspect of the present invention.

In operation, the following process occurs in accordance with one example embodiment of the present invention, and as illustrated in FIG. 9, as well as with reference to FIGS. 1-8. The well-mixed mixture 15 is supplied to the supply hopper 78. The motor 80 rotates the second plate 86 at a desired rate. It has been found with most powder particulate solid mixtures that a rate of between 2 RPM and 20 RPM is appropriate to keep a steady flow, but to avoid going too fast and causing the mixture 15 to sweep past the discharge aperture 84. One of ordinary skill in the art will appreciate that the specific RPM of the second plate 86 is based at least in part on the size of the particles in the mixture 15 and their respective cohesive strength. In general, it is preferable to produce a substantially steady stream of mixture flowing to the channel hopper 12. Thus, if the RPM of the second plate 86 is too slow, a pulsed output would result and this would be undesirable for most applications. However, one of ordinary skill will appreciate that such pulsed operation is achievable with the present invention, thus such action is not beyond the scope of the present invention.

The mixture passes through the supply aperture 102 of the fixed top plate 100 to the supply port 96 in the fixed cam plate 92. The mixture 15 continues through to the deposition aperture 98 and as the second plate 86 rotates, the mixture 15 is deposited on the top of the second plate 86 in a deposition trail having a uniform cross-section shaped similarly to the shape of the deposition aperture 98. In the example embodiment, the deposition aperture 98 maintains an arch shape, but any appropriate shape may be used. The second plate 86 continues its rotation and the deposition trail brushes along the contoured periphery 94 of the fixed cam plate 92. As the deposition trail of the mixture 15 continues around the contoured periphery 94 it is progressively pushed radially outwardly until it eventually reaches and falls through the plurality of pass through apertures 88 in the second plate 86. The second plate 86 continues rotation and pushes the mixture 15 in the pass through apertures 88 to the discharge aperture 84, where the mixture 15 falls through to the fill tube 104 and then into the channel hopper 12 generally at the fill region 36. This entire supply process is done with minimally-shearing action that provides a substantially steady flow rate of the mixture 15 into the channel hopper 12.

The channel hopper 12, prior to the introduction of the mixture 15, is pivoted up on the end of the third wall 24 to create a slope on the third wall of about 5 degrees from vertical (see FIG. 9, step 1, angle P). The slope in the pivoted position is closer to vertical than the slope of the third wall 24 when the channel hopper 12 is sitting level, without pivoting. As the mixture 15 passes through the fill tube 104 it makes minimal contact with the third wall 24 of the channel hopper 12 and slides down the third wall 24 until impacting either the channel blocking portion of the shuttle 50 (or piston channel block 58), or as the mixture collects, other already deposited mixture 15. The mixture 15 eventually begins avalanching down toward the fourth wall 26 as the channel hopper 12 fills with mixture (see FIG. 9, step 2). The angle of repose R of the mixture can be visually tracked with the angle of repose markings 34 if desired.

Once the mixture 15 substantially fills the channel hopper 12, the feeder mechanism 16 is shut down to halt the flow of the mixture 15 to the channel hopper 12. If the channel hopper 12 was pivoted upward for the filling operation, the channel hopper 12 is moved back down to an un-pivoted condition, where the collector 14 is substantially horizontal (see FIG. 9, step 3). The testing apparatus 10 is then ready for the acquisition of samples from the channel hopper 12. As previously discussed, several different mechanisms and methods can be utilized to obtain samples from the channel hopper 12. For purposes of this operational description, the embodiment depicted in FIG. 6 will be referenced.

During the fill operation, the piston channel block 58 is in place completely filling the first receptacle 62, creating the channel block configuration. This enables the mixture 15 to collect in the channel hopper 12. When the fill operation is complete and it is time for sampling to begin, the piston channel block 58 lowers to reveal the first receptacle 62. It shall be noted that the piston does not lower beyond the bottom surface of the first receptacle 62. Thus, there are no gaps formed between the piston channel block 58 and the first receptacle 62. Rather, a chamber is formed within the first receptacle 62, with the only opening being on the topside of the first receptacle 62 allowing mixture 15 to flow from the channel hopper 12 to the first receptacle 62. The first shuttle 60 (in its first position during the fill operation and the lowering of the piston channel block 58), together with the piston channel block 58 and the second shuttle 64, then slides to a second position. At this second position, the piston channel block 58 and second shuttle 64 remain fixed in place. The first shuttle 60 is then moved to a third position, whereby the first receptacle 62 overlaps with the plurality of sample receptacles 18 in the third shuttle 68. The mixture 15 flows from the first receptacle 62 to the plurality of sample receptacles 18 (see FIG. 9, step 4). The plurality of sample receptacles 18 are walled off between one another, such that sections of the channel hopper 12 can be identified and sectioned out for analytical purposes. The number of sample receptacles utilized is reflective of the level of granularity or resolution desired for the particular test. The sample size is important because it can be customized to equal that needed for a particular analytical test, and thus obviate the need for riffling and/or sub-sampling, which can skew the results. If two sample receptacles are utilized, the granularity or resolution is very low, and if twenty or thirty sample receptacles are utilized, the granularity or resolution is quite high. The number of sample receptacles can range from one to a maximum. The maximum number of sample receptacles is limited only by the ability of the mixture 15 to fit in each sample receptacle. If the width of the sample receptacle is so small or narrow as to not allow all sizes of solid particles in the mixture to fit within the sample receptacle, then the number of sample receptacles must be reduced until all particles can fit (alternatively, the width of the discharge opening 30 and total width of the plurality of sample receptacles can be increased with a re-designed testing apparatus).

Once the plurality of sample receptacles 18 are filled with the mixture 15, the third shuttle 68 (in its first position during the transfer of the mixture 15 to the plurality of sample receptacles 18) slides toward a second position. As the third shuttle 68 slides, each individual sample receptacle of the plurality of sample receptacles 18 comes across one of the plurality of staggered apertures 72 in the fixed plate 70. As each sample receptacle overlaps each staggered aperture, the mixture 15 flows from the sample receptacle to one of the plurality of collection containers 74 (see FIG. 9, step 5). Thus, each collection container (1A, 1B, 1C, 1D, 1E) repeatedly receives mixture samples from a same vertical column of mixture from the channel hopper 12. Additionally, the plurality of collection containers 74 can be emptied, or new containers added, and their contents quantified and logged so that each horizontal row of sample taken from the mixture 15 in the channel hopper 12 can be identified. Referring to FIG. 9, (step 4), the vertical and horizontal gradations indicate each sample section that can be attained, identified, quantified, and tested, using the testing apparatus 10 of the present invention.

The testing apparatus 10 of the present invention, and corresponding method of use, provides a user with the ability to simulate the internal conditions of a particulate solid collection within a storage hopper. The amount of particulate solid mixture sample required to perform the test and obtain valid results is substantially less than the amount of mixture stored in the hopper being simulated (on the order of 1600 Kg). A typical testing apparatus may hold on the order of 35 grams (or about 70 ml) of sample mixture. One of ordinary skill in the art will appreciate that the precise weight quantifiers of the hopper being simulated and the testing apparatus are merely exemplary. The present invention is intended to relate generally to the provision of a testing apparatus that requires substantially less particulate solid mixture sample amounts relative to the storage bin or hopper undergoing segregation testing. Thus, in instances where the mixture is formed of relatively expensive material, the smaller sample sizes (relative to the volume of material required in previous segregation test methods) are highly advantageous, because the overall costs of the segregation testing, especially with regard to material, are dramatically reduced relative to other testing methods. Furthermore, the testing apparatus 10 provides a substantially uniform flow of the mixture as it passes through the channel hopper 12 for sampling, thus making the testing apparatus 10 highly accurate in testing the conditions inside a larger hopper collecting the mixture with regard to the occurrence of sifting segregation. Also, the sample size (as collected from the tester) is important because it can be customized to equal that needed for a particular assay, and thus obviate the need for riffling and/or sub-sampling, which can skew the results In addition, the testing apparatus of the present invention makes use of the feeder mechanism 16, which provides a steady minimally-shearing supply of the mixture to the channel hopper 12. The feeder mechanism can vary in speed, thus varying flow rate of the mixture as desired. The feeder mechanism further operates with minimal sifting segregation of the mixture as it passes through the feeder mechanism to the channel hopper 12. Thus, the feeder mechanism provides minimal disruption of the mixture from the supply hopper, but enables regulation and control of the mixture feed to the channel hopper.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. It is intended that the present invention be limited only to the extent required by the appended claims and the applicable rules of law.

What is claimed is:

1. A method of uniformly supplying a mixture of particulate solids, the method comprising:

receiving a supply of the mixture from a supply source;

directing the mixture to a deposition aperture configured to receive the mixture and deposit the mixture on a rotating plate in the form of a deposited trail as the rotating plate rotates;

displacing the deposited trail radially and progressively outwardly along the rotating plate to a plurality of pass through apertures disposed in the plate;

discharging the mixture from the plurality of pass through apertures and through a discharge aperture;

wherein displacing the deposited trail comprises using a fixed cam plate having a contoured periphery configured to displace the deposited trail radially and progressively outward to the plurality of pass through apertures of the rotating plate as the rotating plate rotates, supplying the mixture forming the deposited trail to the discharge aperture.

2. The method of claim 1, wherein the supply source comprises a bin or hopper.

3. The method of claim 1, wherein the deposition aperture is disposed in the fixed cam plate slidably mounted over the rotating plate.

4. The method of claim 1, wherein displacing the deposited trail comprises forming the deposited trail on the rotating plate with a uniform cross-sectional area.

5. The method of claim 1, wherein the cam plate is configured to displace the deposited trail radially and progressively outward with minimal shearing of the mixture forming the deposited trail.

6. The method of claim 1, further comprising rotating the rotating plate at a rate that at least substantially hinders the mixture from arching over the plurality of pass through apertures.

7. The method of claim 1, further comprising rotating the rotating plate at a rate of between about 2 RPM and about 20 RPM.

8. The method of claim 1, further comprising providing a motor driving the rotating plate.

9. The method of claim 1, wherein the feeder supplies a substantially constant stream of the mixture through the discharge aperture.

* * * * *